United States Patent [19]
Collins

[11] Patent Number: 5,941,853
[45] Date of Patent: *Aug. 24, 1999

[54] NEEDLE ASSEMBLIES

[75] Inventor: Michael Norman Collins, Lyminge, United Kingdom

[73] Assignee: Smiths Industries Public Limited Company, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,451

[22] Filed: Jul. 31, 1997

[30] Foreign Application Priority Data

Aug. 16, 1996 [GB] United Kingdom ............... 9617269
Aug. 16, 1996 [GB] United Kingdom ............... 9701668

[51] Int. Cl.⁶ .................................................. A61M 19/00
[52] U.S. Cl. .......................... 604/165; 604/158; 604/534
[58] Field of Search ..................................... 604/158, 164, 604/165, 160, 239, 264, 533, 535, 536, 534

[56] References Cited

U.S. PATENT DOCUMENTS

| | | |
|---|---|---|
| 4,233,974 | 11/1980 | Desecki et al. . |
| 4,518,383 | 5/1985 | Evans . |
| 4,609,370 | 9/1986 | Morrison . |
| 5,057,085 | 10/1991 | Kopans . |
| 5,085,631 | 2/1992 | Leighton . |
| 5,106,376 | 4/1992 | Mononen et al. . |
| 5,160,323 | 11/1992 | Andrew . |
| 5,232,442 | 8/1993 | Johnson et al. . |
| 5,250,035 | 10/1993 | Smith et al. . |
| 5,279,570 | 1/1994 | Dombrowski et al. . |
| 5,304,141 | 4/1994 | Johnson et al. . |
| 5,312,375 | 5/1994 | Gurmarnik . |
| 5,425,718 | 6/1995 | Tay et al. . |
| 5,470,318 | 11/1995 | Griffith, III et al. . |
| 5,480,389 | 1/1996 | McWha et al. .................... 604/165 |
| 5,514,100 | 5/1996 | Mahurkar . |

FOREIGN PATENT DOCUMENTS

| | | |
|---|---|---|
| 0 564 859 | 10/1993 | European Pat. Off. . |
| 0696437A2 | 2/1996 | European Pat. Off. . |
| 295 03 750 U | 6/1995 | Germany . |
| 2309170 | 12/1996 | United Kingdom . |
| 90/14124 | 11/1990 | WIPO . |

*Primary Examiner*—Wynn Wood Coggins
*Assistant Examiner*—A. T. Nguyen
*Attorney, Agent, or Firm*—Pollock, Vande Sande & Amernick

[57] ABSTRACT

A spinal-epidural needle assembly has a rearwardly-extending sleeve on the epidural needle that is rotatable to a limited extent on its hub and that has a series of circumferentially-extending ribs on its outer surface. The spinal needle has a collar extending forwardly from its hub and slidable along outside of the sleeve of the epidural needle. The collar has a small elastomeric pad on its inner surface, which is slidable along a smooth region to one side of the ribbed region. The spinal needle is locked longitudinally relative to the epidural needle by twisting its collar so that the elastomeric pad slides laterally over the ribbed region with the ribs gripping into the pad.

10 Claims, 3 Drawing Sheets

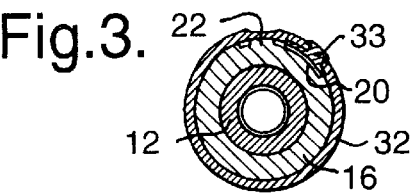
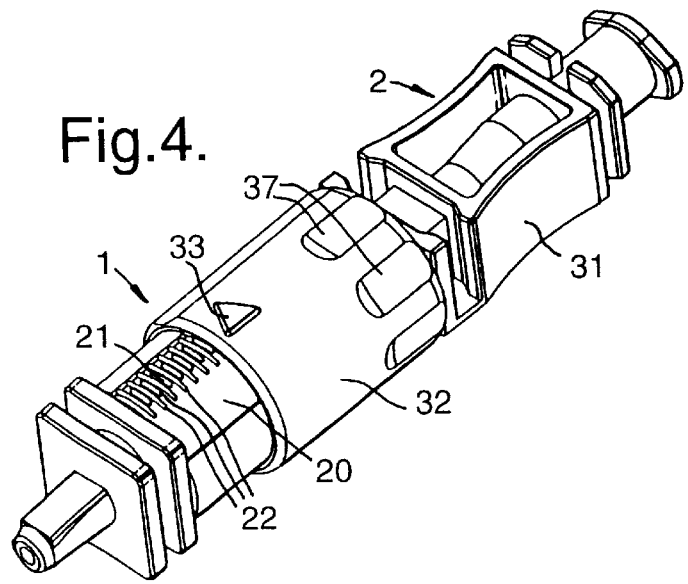
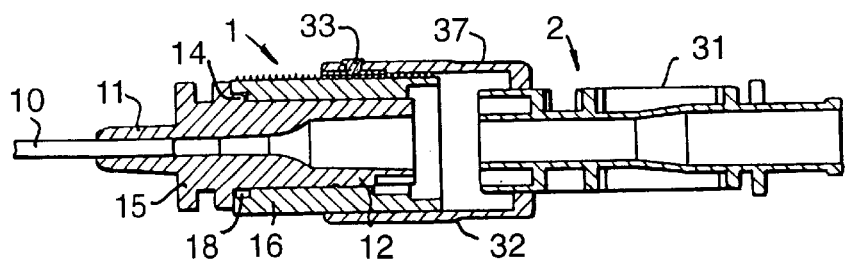
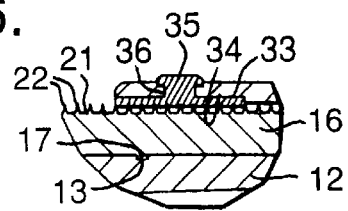

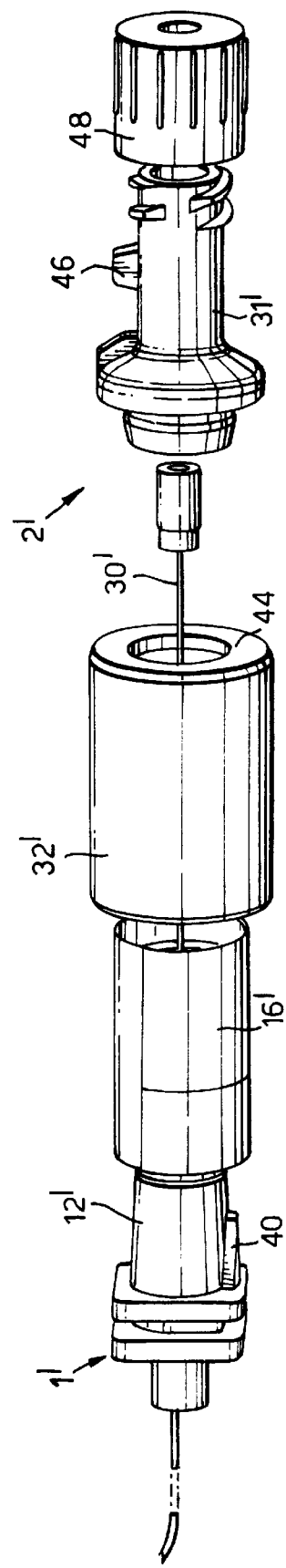
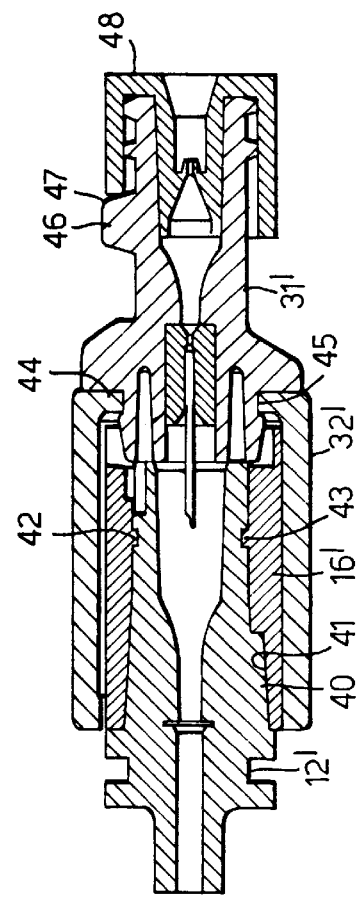
Fig.7.
Fig.8.

NEEDLE ASSEMBLIES

BACKGROUND OF THE INVENTION

This invention relates to needle assemblies.

The invention is more particularly concerned with spinal-epidural needle assemblies.

Spinal-epidural needle assemblies are used for the administration of spinal and epidural anaesthetic fluid. The epidural needle is inserted, in the usual way, into the epidural space. A spinal needle is then inserted through the epidural needle until its tip punctures the dura and enters the subarachnoid space. A syringe is attached to the machine end of the spinal needle and spinal anaesthetic is administered through the spinal needle to produce a rapid but short-lived anaesthetic block. The spinal needle is then removed, leaving the epidural needle in position. An epidural catheter is inserted through the epidural needle so that its patient end is located in the epidural space. The needle is then removed, leaving the catheter in position so that anaesthetic fluid can be administered, as necessary, into the epidural space to produce a longer-lasting anaesthetic effect.

Once the tip of the spinal needle has been correctly inserted, its position must be maintained while the anaesthetic fluid is administered. This can be difficult to do because, although the epidural needle is retained relatively securely by the frictional contact with the tissue through which it is inserted, the spinal needle has a relatively low-friction engagement with the bore of the epidural needle. The anaesthetist must hold the spinal needle during connection of the spinal needle to the syringe and during the administration of the spinal anaesthetic. If the needle should slip, there is the risk of it puncturing the distal wall of the subarachnoid space or of it being pulled out into the epidural space.

Various proposals have been suggested for arrangements by which the spinal needle can be fixed relative to the epidural needle once the spinal needle has been correctly inserted. In Anaesthesia 1990: 45: 593–594 and Acta Anaesthesiologica Scand 1994: 38: 439–441, J Simsa describes a metal screw clamp attached to the epidural needle hub by which the spinal needle can be fixed in position. In EP 0564859 A there is described an assembly where the spinal needle makes a bayonet-like connection with the epidural hub so that the two can be locked together, but this only enables the spinal and epidural needles to be fixed at one location. EP 0696437 describes an assembly in which the spinal needle hub has a resilient locking tab that engages between a series of teeth formed on an extension of the epidural hub. This arrangement requires the user to hold the tab in the released position while inserting the spinal needle; also, the space between the teeth limits the precision with which the spinal needle can be locked in position.

BRIEF SUMMARY OF THE INVENTION

It is an object of the present invention to provide an improved needle assembly.

According to the present invention there is provided a needle assembly comprising a first needle and a second needle insertable within the first needle, the first needle having a hub at its rear end with a rearwardly-extending member, the second needle having a hub at its rear end with a forwardly-extending member, one of said members being insertable within the other said member, the external surface of said one member and the internal surface of the other member having cooperating gripping means, one of said gripping means including an elastomeric member and the other of said gripping means comprising first and second elongate regions extending parallel to one another side-by-side along the respective member, said first region being configured to receive said elastomeric member as a sliding fit along its length, and said second region being provided with surface formations that enable the elastomeric member to be slid laterally, over the surface formations, when the two members are twisted relative to one another but prevent longitudinal movement of the elastomeric member along the second region so that the two members are locked longitudinally with one another.

The surface formations are preferably provided by a series of parallel ribs extending laterally in the second region. The series of ribs may comprise alternate long and short ribs. The rearwardly-extending member is preferably insertable within the forwardly-extending member. The two needles are preferably rotatable relative to one another to a limited extent after being locked longitudinally with one another. The second hub may be rotatable to a limited extend relative to the forwardly-extending member. The elastomeric member is preferably shorter than the second region. The elastomeric member is preferably provided on the inner surface of the other member.

A spinal-epidural needle assembly according to the present invention, will now be described, by way of example, with reference to the accompanying drawings.

BRIEF DESCRIPTION OF THE DRAWINGS

FIG. 3 is a lateral cross section of the assembly in an unlocked state;

FIG. 4 is a perspective view of the assembly in a locked state;

FIG. 5 is a sectional side elevation view of the hubs of the assembly in a locked state;

FIG. 6 shows a part of FIG. 5 to a larger scale;

FIG. 7 is an exploded, perspective view of an alternative assembly; and

FIG. 8 is a sectional side-elevation view of the hubs of the alternative assembly in a locked state.

DETAILED DESCRIPTION OF THE PREFERRED EMBODIMENT

Figure 1:
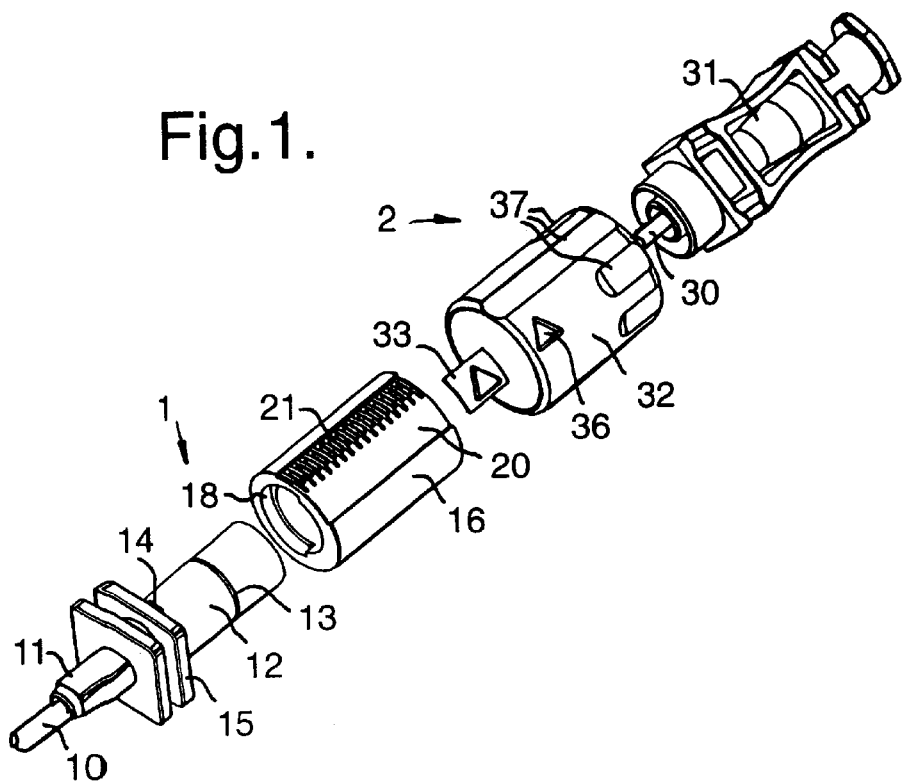
FIG. 1 is an exploded perspective view of the assembly.

With reference first to FIG. 1, the assembly comprises an epidural needle assembly 1 and a spinal needle assembly 2, which can be locked with the epidural needle assembly at various different longitudinal positions.

The epidural needle assembly 1 comprises a conventional epidural, Tuohy needle 10 with a plastics hub 11 bonded at its rear end. The rear end of the hub 11 comprises a rearwardly-extending cylindrical spigot 12 having a circumferential groove 13 about midway along its length. A short stop 14 projects rearwardly from the rear face of a square flange 15 at the forward end of the spigot 12. The epidural needle assembly 1 is completed by a cylindrical sleeve 16 of a rigid plastics material, which is a snap-fit on the spigot 12. The sleeve 16 has an internal rib 17 located to engage the groove 13 on the spigot 12 so as to lock the sleeve against longitudinal movement but to allow it to rotate about the spigot. At its forward end, a channel 18 is formed around the inside of the sleeve 16 to receive the stop 14 on the flange;

the channel only extends around the sleeve by about 180°, so as to limit rotation of the sleeve about the spigot 12 to the same extent. On its external surface, the sleeve 16 has two elongate regions 20 and 21 extending longitudinally side-by-side along the sleeve. One region 20 is smooth and has a slightly smaller radius than the remainder of the sleeve, forming a shallow longitudinal channel. The other gripping region 21 is a continuation of the first region 20 but has a series of outwardly-projecting surface formations in the form of parallel, shallow gripping ribs 22 extending circumferentially across the region. The ribs 22 are triangular in profile with a sharp apex and are about 0.25 mm high. The ribs 22 alternate between short and long ribs at a pitch of 0.5 mm.

The spinal needle assembly 2 comprises a conventional spinal needle 30 and hub 31 of the conventional kind but with a hollow cylindrical collar 32 fixedly bonded to the hub and extending forwardly from it. The length of the collar 32 is the same as that of the sleeve 16 and its internal diameter is the same as the external diameter of the sleeve so that it is a close sliding fit on the sleeve 16. The collar 32 carries a small gripping pad 33, in a shallow recess 34 (FIG. 6) on the inside of the collar 32 at its forward end. The pad is of an elastomeric material, such as natural rubber, polyurethane or any other material with which the ribs will grip. The pad 33 is held in position by means of an enlarged head 35 on the pad 33, which is a snap fit in an aperture 36 through the wall of the collar. Alternatively, the pad could be moulded directly onto the collar, such as by injection moulding from a lower melting temperature plastics material. The thickness of the pad 33 and the depth of the recess 34 are such that the inner surface of the pad projects in beyond the inner surface of the collar. The outside of the collar 32 is shaped with knurls 37 to improve grip.

Figure 2:
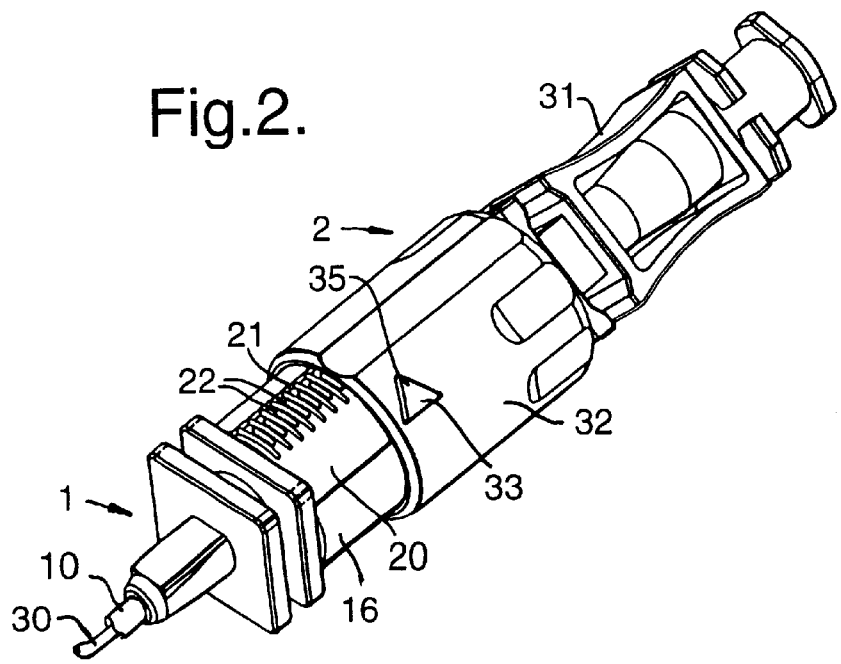
FIG. 2 is a perspective view of the assembly in an unlocked state.

In use, the epidural needle 10 is inserted into the epidural space, in the usual way. The spinal needle 30 is then inserted through the epidural hub 11 and into the epidural needle 10. When the forward end of the collar 32 approaches the rear end of the sleeve 16, the user ensures that the sleeve is rotated fully clockwise, against the stop 14, and that the spinal needle 30 is oriented with the elastomeric gripping pad 33 aligned with the smooth channel 20 in the sleeve 16. In this orientation, the spinal needle assembly 2 can slide freely into the epidural needle assembly 1 to the desired extent, as shown in FIGS. 2 and 3. The ribs 22 on the sleeve 16 serve as convenient depth markers and numbers could be printed alongside the ribs in the channel 20. When the spinal needle assembly 2 has been inserted to the desired extent, it is locked in position relative to the epidural needle assembly 1 simply by twisting spinal needle assembly through about 45° relative to the epidural needle assembly, as shown in FIGS. 4, 5 and 6. This moves the elastomeric pad 33 laterally from the smooth channel 20 across the ribs 22, which bite into and grip the underside of the pad. The circumferential orientation of the ribs 22 enables the pad 33 to move laterally, along the length of the ribs, but prevents longitudinal displacement, transversely of the ribs, so that the spinal needle assembly 2 is locked longitudinally relative to the epidural needle assembly 1. Because the sleeve 16 is rotatable on the epidural hub 11, it is still possible to rotate the spinal needle assembly 2 anticlockwise through 180° without releasing the locking engagement of the pad 33. When it is necessary to remove the spinal needle assembly 2, it is twisted through 180° until the stop 14 prevents further rotation of the sleeve 16. The collar 32 is then twisted through a further 45° anticlockwise so that the pad 33 moves laterally relative to the ribbed region 21 and into the smooth channel 20, thereby enabling the spinal needle assembly 2 to be pulled rearwardly out of the epidural needle assembly 1.

The grip between the elastomeric pad and the ribs has the advantage that locking can be achieved at any longitudinal position, enabling infinitely variable positioning of the spinal needle relative to the epidural needle.

The elastomeric pad 33 is relatively short compared with the length of the collar 32 so that the entire length of the pad is gripped by the gripping ribs 22 at all longitudinal positions of the collar relative to the sleeve, except at extreme rear positions of the collar. This ensures that the same force is required to lock and unlock the two assemblies 1 and 2, at all longitudinal positions. In an alternative arrangement, the elastomeric pad could extend along the entire length of the collar 32. In such an arrangement, a constant locking force could be achieved by providing locking ribs along only a short part of the sleeve 16, at its rear end, so that the same number of ribs are gripped at all longitudinal positions of the collar. Various other modifications are possible, for example, the elastomeric member could be provided on the outer surface of the inner locking member instead of on the inner surface of the outer locking member. In such an arrangement, the ribs or other gripping surface formations would be provided on the inside of the outer locking member.

In the above arrangement, the sleeve 16 having the gripping region 21 is rotatable to a certain extent about the epidural hub 11, to enable orientation of the spinal needle 30 as desired. Although this has certain advantages, it does mean that the sleeve 16 has to be rotated to its furthest extent in opposite directions, both when locking and unlocking the collar 32. If the sleeve 16 is already fully rotated in the locking direction when the collar 32 is slid into position, it means that the collar only has to be twisted through a relatively small angle to lock. However, to unlock, the user has to twist the collar 32 to rotate the sleeve 16 to its full extent in the opposite direction before the collar can be released from the sleeve. The need to rotate the collar through different angles to achieve locking and unlocking can be confusing.

In the arrangement shown in FIGS. 7 and 8, the sleeve 16' is locked onto the spigot 12' in a way that prevents the sleeve rotating on the spigot. In particular, the spigot 12' has a radially-projecting rib 40, which lies in a corresponding recess 41 on the inside of the sleeve 16'. The outside of the spigot 12' and the inside of the sleeve 16' have cooperating tapers so that the sleeve is a tight fit on the spigot, and they have an engaging ring 42 and recess 43, which are a snap fit together to prevent axial displacement after assembly. The collar 32' has an inwardly-projecting flange 44 at its rear end, which is a snap fit in a channel 45 formed around the outside of the forward end of the spinal needle hub 31'. The engagement of the flange 44 in the channel 45 allows the spinal needle assembly 2' to be rotated relative to the collar 32'. The spinal needle hub 31' is of cylindrical shape and circular section, having a lug 46 projecting radially outwardly. The lug 46 indicates the orientation of the spinal needle 30', since this is fixed with the hub 31', and also locates with a slot 47 in the hub 48 of a stylet assembly (only the hub of which is shown) so that the stylet is correctly oriented at the tip of the spinal needle. The stylet hub 48 is a push fit over the rear end of the spinal needle hub 31'.

In use, the user holds the spinal needle assembly 2' by the collar 32' and aligns this, in the way described earlier, with the sleeve 16' so that the spinal needle assembly can be slid forwardly to the desired position. When this position has been reached, the collar 32' is twisted through about 45° so that its pad engages the gripping region on the sleeve 16'. With the spinal needle assembly 2' locked in this way against axial displacement relative to the epidural needle assembly 1', the spinal needle can be rotated, if desired, by gripping the spinal needle hub 31' and twisting it relative to the collar 32'. To remove the spinal needle assembly 2', the collar 32' is simply twisted back through the same angle so that the grip is released and the spinal needle assembly can be pulled out of the epidural needle assembly. It can be seen that, in this arrangement, locking and unlocking are achieved by twisting through the same angle.

What I claim is:

1. A needle assembly comprising: a first needle having a first hub at its rear end, said first hub having a rearwardly-extending member; and a second needle insertable within said first needle, said second needle having a second hub at its rear end, said second hub having a forwardly-extending member, one of said members being insertable within the other said member, said two members being twistable angularly relative to one another between a locked position and an unlocked position, an external surface of one member and an internal surface of the other member having cooperating gripping surfaces, a first gripping surface on one of said members including a part fabricated of an elastomeric material and the other of said members having first and second elongate regions extending longitudinally, parallel to one another, side-by-side along said other member, said first region being configured to permit said elastomeric material part to slide longitudinally along its length in said unlocked position of said members, and said second region including a second gripping surface adapted to enable the elastomeric material part to be slid laterally over said second gripping surface to cause surface formations on said second gripping surface to bite into the elastomeric material of said part when said two members are twisted relative to one another into said locked position of said members thereby to prevent longitudinal movement of said elastomeric material part along said second region so that said two members are locked longitudinally relative to one another.

2. A needle assembly according to claim 1, wherein said second gripping surface is provided by a series of parallel ribs extending laterally in said second region.

3. A needle assembly according to claim 2, wherein said series of ribs comprises alternate long and short ribs.

4. A needle assembly according to claim 1, wherein said rearwardly-extending member is insertable within said forwardly-extending member.

5. A needle assembly according to claim 1, wherein said two needles are rotatable relative to one another to a limited extent after being locked longitudinally with one another.

6. A needle assembly according to claim 1, wherein said second hub is rotatable to a limited extent relative to said forwardly-extending member.

7. A needle assembly according to claim 1, wherein said elastomeric part is shorter than said second region.

8. A needle assembly according to claim 1, wherein said elastomeric part is provided on an inner surface of said other member.

9. A spinal-epidural needle assembly comprising: an epidural needle having a first hub at its rear end, said first hub having a rearwardly-extending member; and a spinal needle insertable within said epidural needle, said spinal needle having a second hub at its rear end, said second hub having a forwardly-extending member, one of said members being insertable within the other said member, said members being twistable angularly relative to one another between a locked position and an unlocked position, an external surface of said one member having a series of parallel ribs extending laterally, and an internal surface of said other member having a part fabricated of an elastomeric material, said other member being slidable longitudinally relative to said one member when said two members are in their unlocked position, and said elastomeric material part being slidable laterally, along the ribs, when said two members are twisted relative to one another into their locked position so as to cause said ribs to bite into a surface of the elastomeric material in said part and thereby lock said spinal needle against longitudinal movement relative to said epidural needle.

10. A spinal-epidural needle assembly comprising: an epidural needle having a first hub at its rear end, said first hub having a cylindrical sleeve mounted thereon for limited rotation; and a spinal needle insertable within said epidural needle, said spinal needle having a second hub at its rear end, said second hub having a collar arranged to embrace said sleeve on said first hub, said needle assembly having an unlocked configuration wherein said collar is slidable longitudinally relative to said sleeve, an external surface of said sleeve having a series of parallel, circumferentially-extending ribs, said collar having a part fabricated of an elastomeric material, and said collar being rotatable relative to said sleeve to change the configuration of said needle assembly from said unlocked configuration into a locked configuration wherein said elastomeric material part is displaced circumferentially along said ribs while said circumferentially-extending ribs bite into a surface of said elastomeric material to lock the spinal needle against longitudinal movement relative to said epidural needle.

* * * * *